United States Patent
Murayama

(10) Patent No.: US 11,094,062 B2
(45) Date of Patent: Aug. 17, 2021

(54) AUTO COMPARISON LAYOUT BASED ON IMAGE SIMILARITY

(71) Applicant: FUJIFILM MEDICAL SYSTEMS U.S.A., INC., Lexington, MA (US)

(72) Inventor: Masashi Murayama, Setagaya (JP)

(73) Assignee: FUJIFILM MEDICAL SYSTEMS U.S.A., INC., Lexington, MA (US)

( * ) Notice: Subject to any disclaimer, the term of this patent is extended or adjusted under 35 U.S.C. 154(b) by 0 days.

(21) Appl. No.: 16/050,968

(22) Filed: Jul. 31, 2018

(65) Prior Publication Data

US 2020/0043167 A1 Feb. 6, 2020

(51) Int. Cl.
    *G06T 7/00*     (2017.01)
    *G16H 50/70*     (2018.01)
    *G16H 30/40*     (2018.01)

(52) U.S. Cl.
    CPC .......... *G06T 7/0014* (2013.01); *G16H 30/40* (2018.01); *G16H 50/70* (2018.01); *G06T 2200/24* (2013.01)

(58) Field of Classification Search
CPC ... G06T 7/0014; G06T 2200/24; G16H 50/70; G16H 30/40
USPC ......................................................... 382/128
See application file for complete search history.

(56) References Cited

U.S. PATENT DOCUMENTS

| | | | |
|---|---|---|---|
| 7,890,870 B1 * | 2/2011 | Metiers | H04L 67/36 715/736 |
| 2002/0046386 A1 * | 4/2002 | Skoll | G06T 7/0006 716/102 |
| 2013/0080425 A1 * | 3/2013 | Kwete | G16H 10/60 707/723 |
| 2018/0293773 A1 * | 10/2018 | Kohle | G06T 11/60 |

* cited by examiner

*Primary Examiner* — Wednel Cadeau
(74) *Attorney, Agent, or Firm* — Heslin Rothenberg Farley & Mesiti P.C.

(57) ABSTRACT

A method and apparatus are disclosed herein for automatically creating a comparison layout using series matching based on image similarity. In one embodiment, a method for displaying series images in a graphical user interface (GUI) comprises receiving a current study and one or more previously-created studies, each of the current study and the one or more previously-created studies having at least one images series; performing, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies; and creating a comparison layout in the GUI with at least one image from one image series of the current study adjacent to at least one image from an image series of at least one of the one or more previously-created studies.

25 Claims, 9 Drawing Sheets

Receive a current study and one or more previously-created studies, where each of the current study and the one or more previously-created studies having at least one images series
1001

Perform, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies
1002

Create a comparison layout in the GUI with at least one image from one image series of the current study adjacent to at least one image from an image series of at least one of the one or more previously-created studies
1003

Cause the display to display an amount of similarity on the GUI for one or more studies in the previously-created studies
1004

FIG. 10

Receive a current study and displaying at least one image from at least one image series in the study
1101

Obtain one or more previously-created studies in response to displaying one or more images of the current study
1102

Perform, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies
1103

Generate a rank similarity order indicating comparative similarity between a plurality of image series of each of the previously-created studies and a current image series of the current study being viewed
1104

Create a comparison layout in the GUI with at least one image from one image series of the current study adjacent to at least one image from an image series of at least one of the one or more previously-created studies
1105

Display the ranking similarity order in the GUI with selectable user interface elements to enable selection of each ranked series in the previously-created studies to cause one or more images of a selected study to be displayed in the comparison layout with one or more images from the current study
1106

FIG. 11

AUTO COMPARISON LAYOUT BASED ON IMAGE SIMILARITY

FIELD OF THE INVENTION

Embodiments of the present invention relate to the field of medical imaging analysis; more particularly, embodiments of the present invention relate to automatically generating a layout of medical images in which the medical images are selected and displayed based on image similarity.

BACKGROUND

Current medical imaging technology includes the use of medical images such as, among others, x-rays, mammograms, computerized tomography (CT) scans, magnetic resonance images (Mills), positron emission tomography (PET) scans and ultrasound images. These images are generated by medical imaging modalities.

Medical facilities are more readily adopting electronic displays for displaying medical images. Often after an imaging modality takes medical images, those images are included in a study that is sent to a picture archiving and communication system (PACS). The PACS is a medical imaging technology that allows access to images from multiple locations. Doctors and/or other medical professionals obtain studies that are stored in the PACS and review, or read, the images in the studies to obtain clinical information about their patients. If a patient has a serious medical condition that needs urgent attention, the doctor is often able to make that determination by reviewing the images in the study.

In some case, if patient has a prior study, a physician may want to compare it with latest study in order to make a treatment assessment, diagnosis, etc. The comparison may be made by laying out images in the current study and images in a prior study side-by-side. A mammography reader routinely uses such a comparison layout.

However, in some cases, it's hard to match a series of the current study and most relevant series of one or more studies created prior to the current study. In its studies, mammography uses a normalized series description, so it's easy for mammography software to match such image series of multiple studies. Computed Tomography (CT) and Magnetic Resonance Imaging (MRI) use a series description for images series as well, but it's not normalized. Therefore, matching images series in studies with CT and MR images is much more difficult.

Ultrasound for Cardiovascular (CV) is the most challenging modality in which to match image series from multiple studies. In the case of CV, each study has dozens of series, and they lack any series description. Therefore, it is even more difficult to match a series from a current study with those of a previously-created study. Currently in the case of CV, to match a series from multiple studies, a user visually checks the series one by one and performs a layout of the two matching series manually. That is, the user manually creates the layout of such similar series by dragging and dropping thumbnails, which is very time consuming.

SUMMARY OF THE INVENTION

A method and apparatus are disclosed herein for automatically creating a comparison layout using series matching based on image similarity. In one embodiment, a method for displaying series images in a graphical user interface (GUI) comprises receiving a current study and one or more previously-created studies, each of the current study and the one or more previously-created studies having at least one images series; performing, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies; and creating a comparison layout in the GUI with at least one image from one image series of the current study adjacent to at least one image from an image series of at least one of the one or more previously-created studies.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 10 is a flow diagram of one embodiment of a process for displaying series images in a graphical user interface (GUI).

FIG. 11 is a flow diagram of an alternative embodiment of a process for displaying series images in a graphical user interface (GUI).

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems, methods, and GUIs for displaying at least one medical, or healthcare, image next to at least one other medical image for a patient simultaneously. The systems, methods, and GUIs of the present invention not only have the ability to display images simultaneously, side-by-side in a single viewer, but also creating a comparison layout displaying at least one medical image of a series in a current healthcare study and at least one medical image from a series of a study created prior to the current study (i.e., a previously-created study) for a patient simultaneously by performing series matching based on image similarity. Having briefly described an overview of the present invention, embodiments of the invention will be discussed with reference to FIGS. 1-12.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
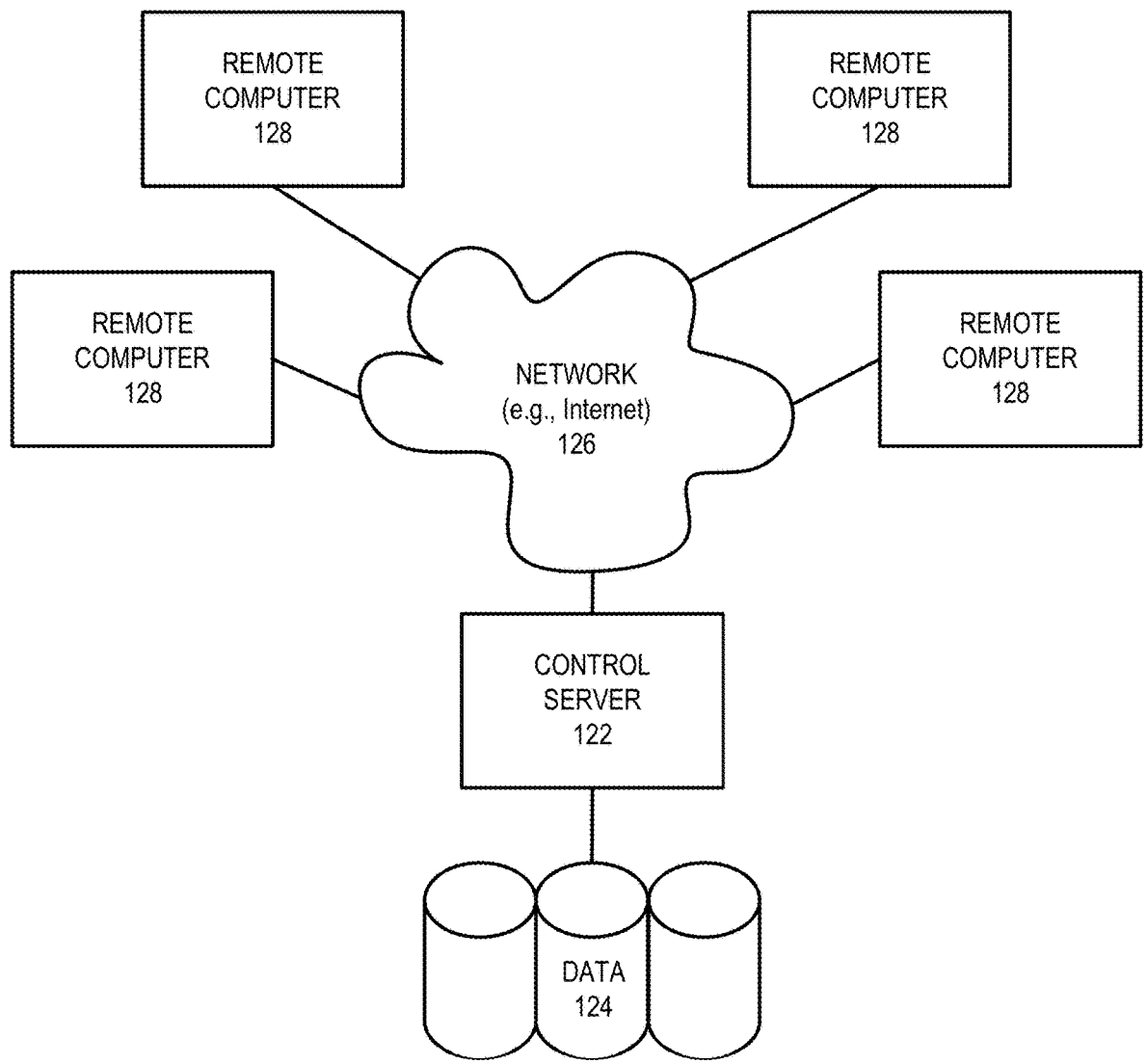
FIG. 1 illustrates an exemplary a medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22. The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
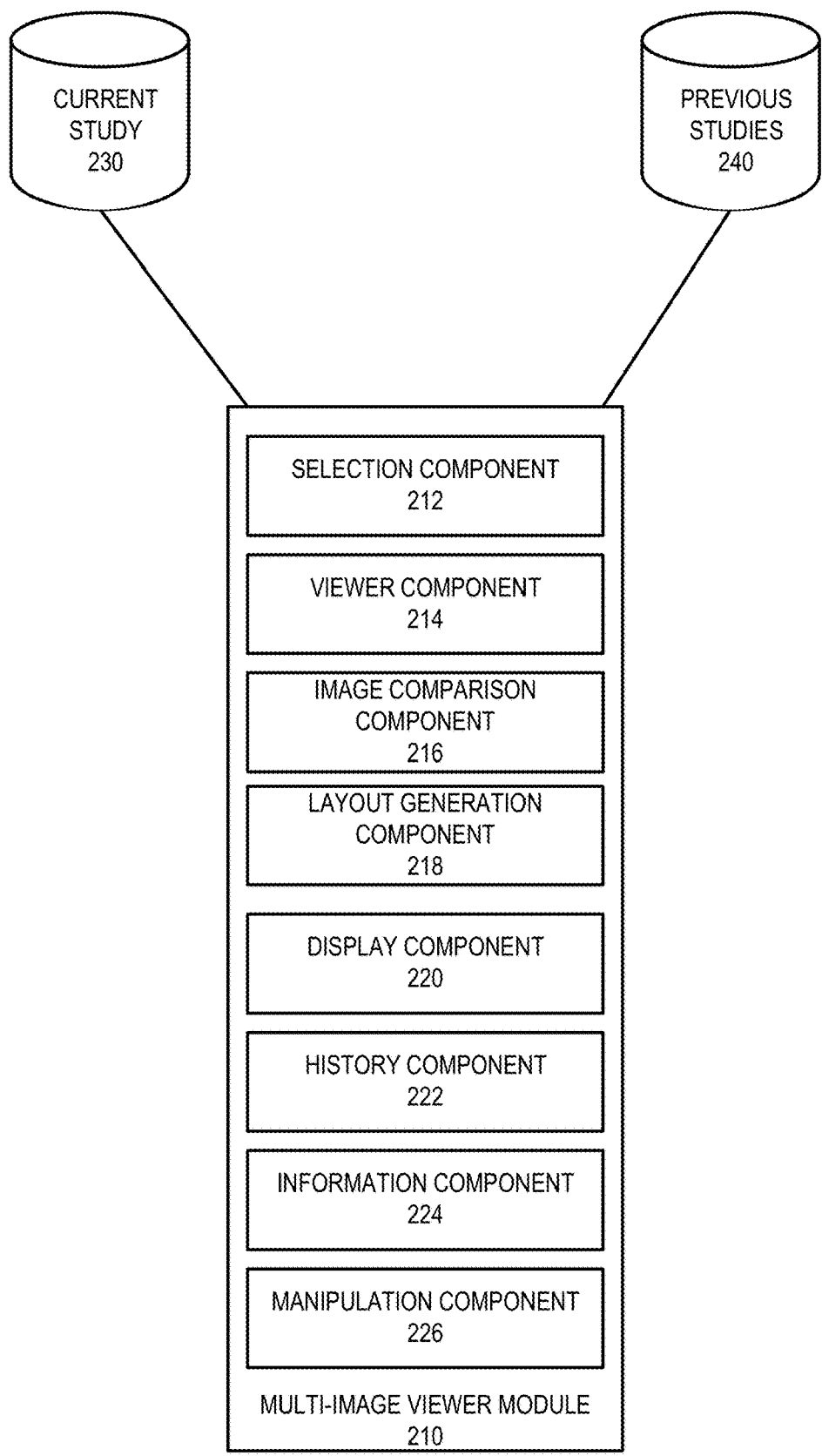
FIG. 2 is a block diagram showing one embodiment of a computing system architecture for automatically creating a comparison layout displaying at least one medical image of a series in a current healthcare study and at least one medical image from a series of a previously-created study for a patient simultaneously.

With reference to FIG. 2, a block diagram is illustrated that shows an exemplary computing system architecture for automatically creating a comparison layout displaying at least one medical image of a series in a current healthcare study and at least one medical image from a series of a study created prior to the current study (i.e., a previously-created study) for a patient simultaneously by performing series matching based on image similarity. It will be appreciated that the computing system architecture shown in FIG. 2 is merely an example of one suitable computing system and is not intended as having any dependency or requirement related to any single module/component or combination of modules/components.

The computing system includes a multi-image viewer module 210 and one or more databases 230 and 240, storing and maintaining medical images from multiple image series of multiple healthcare studies, both current studies and one or more previous studies. Exemplary medical images include radiology images, laboratory images, pictures, cardiology images, such as ECHO images, and other healthcare images. One of skill in the art will appreciate that the databases may be maintained separately or may be integrated. Databases 230, 240 may contain images that are linked to a patient's electronic medical record (EMR), such that images may be selected from within the EMR and launched and displayed within a single viewer via the multi-image viewer module 210. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); other images; evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Graphical display device 220 may be a monitor, computer screen, project device or other hardware device for displaying output capable of displaying graphical user interfaces.

Multi-image viewer module 210 receives and displays images that are sourced from more than one source, or database. Thus, a single storage repository or a single PACS system is not required. Multi-image viewer module 210 may reside on one or more computing devices, such as, for example, the control server 22 described above with reference to FIG. 1. By way of example, the control server 22 includes a computer processor and may be a server, personal computer, desktop computer, laptop computer, handheld device, mobile device, consumer electronic device, or the like.

Multi-image viewer module 210 comprises selection component 212, viewer component 214, image comparison component 216, layout generation component 218, and display component 220. In various embodiments, multi-image viewer module 210 includes a history component 222, an information component 224, and a manipulation component 226. It will be appreciated that while multi-image viewer module 210 is depicted as receiving healthcare images from a current study 230 and from one or more previous studies 240, multi-image viewer module 210 may receive healthcare images from multiple sources including databases spread across multiple facilities and/or multiple locations. It will also be appreciated that multi-image viewer module 210 may receive healthcare images from the sources described above via links within a patient's EMR.

The selection component 212 receives a selection of more than one healthcare study. A healthcare study comprises one or more series. Each series comprises one or more images depicting the subject of the image from various angles. A list perspective within a multimedia manager provides a list of available studies, images, and other media. A clinician can select the desired items to launch in the viewer. In one embodiment, the selection of desired items may be made within the EMR.

Once the selection component 212 receives the clinician's selection, the viewer component 214 launches the viewer for the selected studies. The image comparison component 216 determines the visual similarity between one or more images of a series in a current study and one or more images in one or more previous studies. The image similarity is used to match a series in the current study with a series in one of the previously-created studies. Once the series are matched, layout generation component 218 creates a comparison layout for display that allows one or more images of the current study to be compared to one or more images of at least one previous study. In one embodiment, layout generation component 218 creates a side-by-side layout with series images of the current and previously-created studies rendered next to each within the same viewer.

The display component 220 displays the one or more images of the current study to be compared to one or more images of at least one previous study in the viewer.

In one embodiment, a history component 222 displays a history of different studies and clinical images associated with the more than one healthcare image. The history component 222 further allows a selection of one or more images from the history to be displayed in the viewer by the display component 220. For example, the selection component 212 may have received a selection from the clinician of a particular study. However, once the display component 220 has displayed the images that comprise that selected study, the history component 222 may display other studies and clinical images that are of particular interest to the clinician. The clinician may then select additional items from the history to launch within the viewer.

In one embodiment, information component 224 displays additional information associated with the more than one healthcare image, the history, or a combination thereof. The additional information comprises patient identifying information, image related information, study related information, or a combination thereof. Such additional information may also include time related information.

In one embodiment, a manipulation component 226 allows a clinician to manipulate a display of a healthcare image. For example, a clinician may determine that the image as it is rendered within the viewer is not large enough to see a desired level of detail. The clinician may zoom in or out and the manipulation component 226 manipulates the display of the image accordingly. Similarly, the clinician may desire to pan an image and the manipulation component 226 manipulates the image display accordingly.

Figure 3:
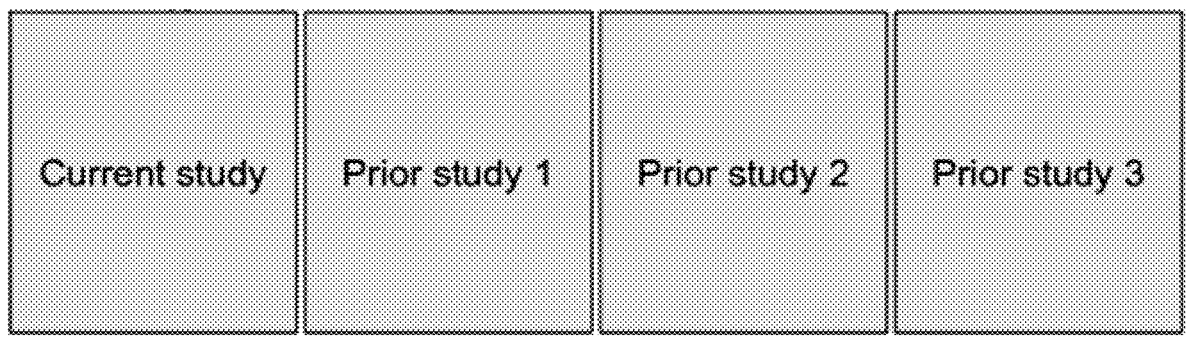
FIG. 3 illustrates an example of a layout for comparison.

FIG. 3 illustrates an example of a layout for comparison. The layout may be included in a GUI or other viewer on a display. The GUI or viewer may be displayed as part of a browser window.

Figure 4:
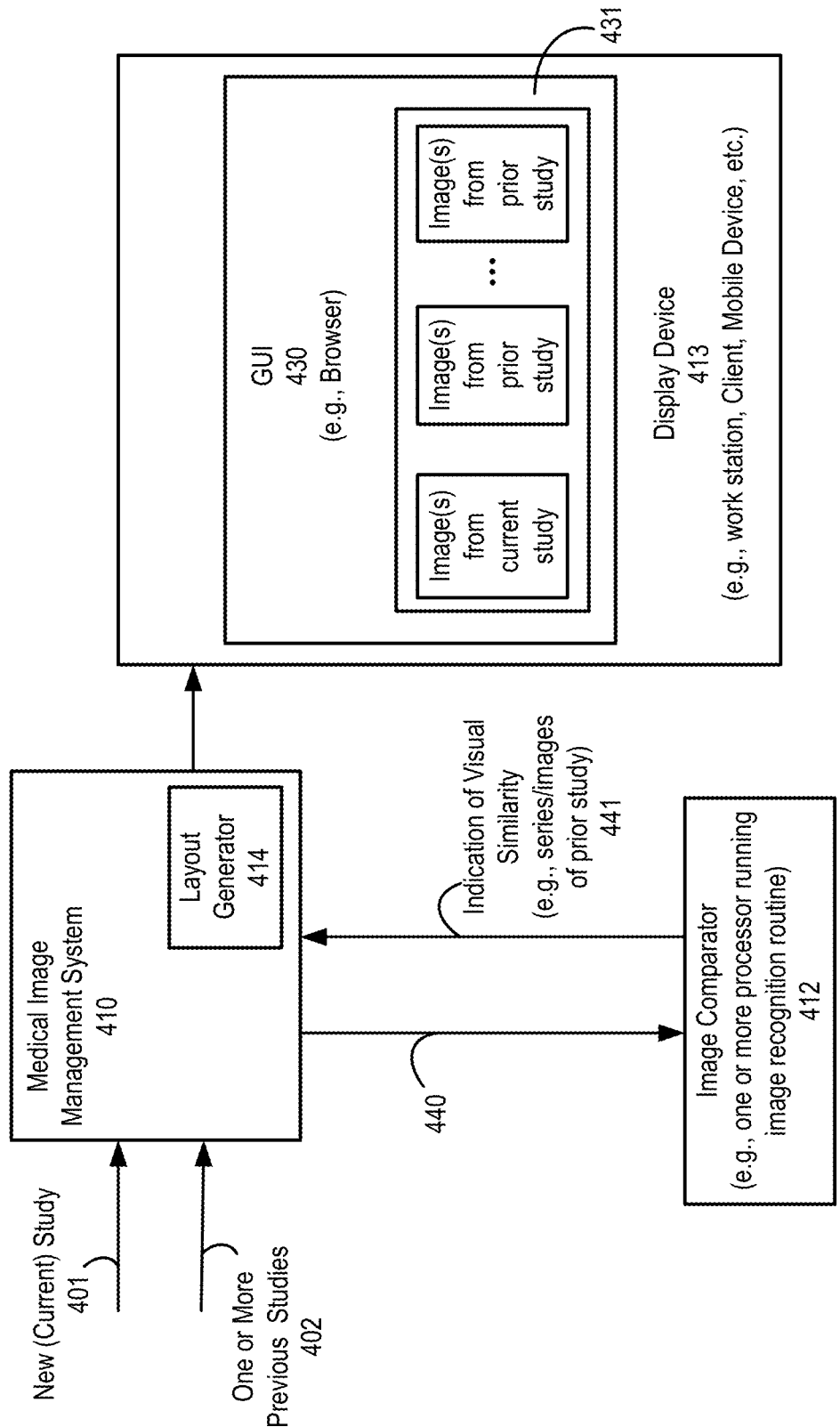
FIG. 4 is a data flow diagram of one embodiment of an automatic comparison layout generation process being performed with a medical image management system.

FIG. 4 is a data flow diagram of one embodiment of an automatic comparison layout generation process being performed with a medical image management system. Medical image management system 410 allows medical images to be accessed, displayed, and revised by individuals.

Referring to FIG. 4, a new, or current, study 401 of a patient is received by a medical image management system 410 along with one or more previously-created patient studies 402. In one embodiment, current study 401 is sent from a medical imaging modality that performs medical imaging (e.g., X-ray radiography, magnetic resonance imaging, ultrasound, endoscopy, tactile imaging, thermography, nuclear medicine functional imaging techniques such as positron emission tomography (PET) and single-photon emission computed tomography (SPECT), etc.). In another embodiment, current study 401 is received from a remotely located image repository (e.g., a picture archiving and communication system (PACS)).

Previously-created studies 402 are obtained from the local storage of medical image management system 410 or one or more remotely located image repositories (e.g., a PACS). Previously-created studies 402 may be obtained in response to a user of medical image management system 410 signaling the medical image management system 410 to obtain such studies for the automatic comparison layout generation process.

After obtaining current study 401 and one or more prior studies 402, image comparator 412 receives the studies (440) and determines image similarly between images of the series to determine visual similarity between the series. In one embodiment, image comparator 412 comprises hardware, software and/or firmware may be configured to analyze medical images perform an image recognition routine to determine the visual similarity.

In one embodiment, the image comparator performs an image recognition algorithm calculates the similarity between series of the current study and those of the prior studies. In one embodiment, the image recognition algorithm performs a structural (e.g., shape) comparison between images in the series of the current and prior studies. In one embodiment, this comparison looks at image characteristics such as color to determine similarity. In another embodiment, this comparison looks at one or more image characteristic that include shapes, size, volume change, etc. Because the studies have a number of images, in one embodiment, the comparison is performed between a subset of images. In one embodiment, the subset includes one image slice from each series. In one embodiment, the one image is a representative image for each series, such as, for example, but not limited to, the middle slice in each series. Thus, in such a case, the image recognition algorithm calculates the visual similarity between the middle slice in each series.

Note that in one embodiment, image comparator 412 is part of medical image management system 410. However, in another embodiment, image comparator 412 is located on a remotely located server(s) and performs the image comparison remotely.

After determining image similarity, image comparator 412 sends an indication 441 of which series are visually similar. In one embodiment, indication 441 includes information identifying the series and/or image of a series of one or more prior studies that are determined to be visually similar to the currently displayed series of the current study 401. In one embodiment, indication 441 includes information that specifies the amount of similarity between one or more series of the prior studies 402 and the series of current study 401. In another embodiment, indication 441 specifies an order or rank of each series in each prior study 402 as to the amount of similarity between each series and the currently displayed series of current study 401.

Layout generator 414 receives indication 441 and uses that information to generate a comparison layout 431 in a GUI 9 (or viewer) 430 on display device 413. That is, layout generator 414 uses information from indication 441 to select series from previous studies 402 to be displayed along with the image series from current study 401. In one embodiment, layout generator 414 generates a side-by-side layout with the image series of the current study 401 next to images series from the one or more previous-created studies 402, such as shown in window 431.

Figure 5:
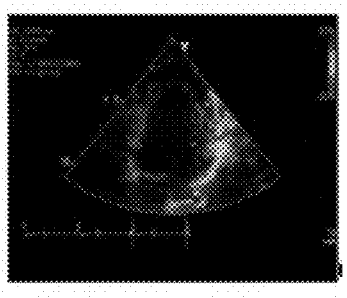
FIG. 5 illustrates an image of a current series that is displayed when a user invokes the auto comparison layout creation function.
Figure 6:
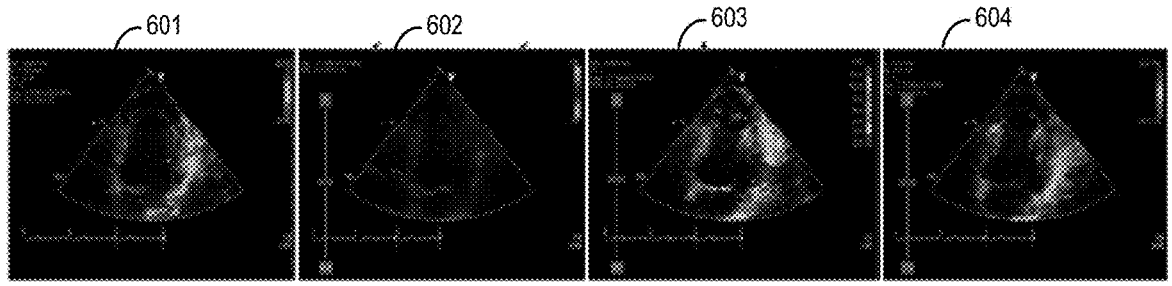
FIG. 6 illustrates another example of an automatically created layout that has an image from a current series and one image from each of a number of prior studies.

FIG. 5 illustrates an image from a series in a current study that is displayed when a user invokes the auto comparison layout creation function. FIG. 6 illustrates an example of an automatically created layout that has the image from a series in a current study 601 being displayed on a screen in the left side of the viewer window, with the most similar image of the series in a first prior study 602 determined to be most visually similar, the most similar image of the series in a second prior study 603 determined to be most visually similar, and the most similar image of the series in a third prior study 604 determined to be most visually similar to the right of current series 601.

Note that the comparison layout of FIG. 6 is merely one example and other comparison layouts may be generated and displayed. For example, in one embodiment in which the user wants a comparison layout such as, a 2×2 layout of images from a current series, a similar set of images from other prior studies may be generated.

Figure 7:
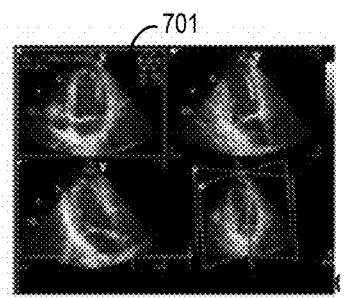
FIG. 7 illustrates four images of a current series that is displayed when a user invokes the auto comparison layout creation function.
Figure 8:
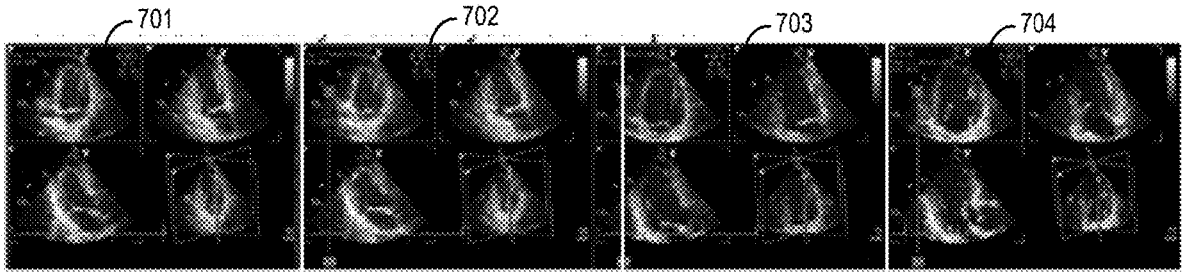
FIG. 8 illustrates another example of an automatically created layout that has four images of a current series and four images from each of a number of prior studies

FIG. 7 illustrates four images 701 of a series of a current study that is displayed when a user invokes the auto comparison layout creation function. FIG. 8 illustrates an example of an automatically created layout that has four images 701 of the series in the current study being displayed on a screen in the left side of the viewer window, with four images 702 of the series in a first prior study determined to be most visually similar, four images 703 of the series in a second prior study determined to be most visually similar, and four images 704 of the series in a third prior study 704 determined to be most visually similar to the right of four images 701.

In one embodiment, the comparison layout is generated automatically when user invokes the auto comparison layout function. In one embodiment, this is invoked by using a GUI element that appears on the display screen. This may be a button, drop-down menu, etc., which is selected by a cursor, stylus, trackpad, or other cursor control device or by touch (in the case of a touch screen display). When invoked, the image viewer utilizes the calculated similarity to select the images that are to appear in the viewer layout. In one embodiment, the viewer layouts the an image from the current study on the left side of a viewer window, and automatically lines up the one or more most similar images from the one or more prior studies on the right side of the image from the current study. This enables the user to compare the images in the created comparison layout.

In one embodiment, as soon as a user invokes the medical image management system to display an image series from a current study, the medical image management system searches for other studies of the patient, to determine if there are prior studies available for the patient. For example, the medical image management system may use a patient identifier, or other patient identification information, to start a search of its memory or remotely-located storage (e.g., PACS) for previously-created studies for the patient. In one embodiment, if one or more such previously-created studies are found, the system prompts the user by displaying a message on the display screen that prior studies are available and asks whether the user wishes to use automatically comparison layout generation to automatically generate and display a comparison layout with an image series from the current study and similar image series from one or more prior studies.

Note that the above examples include an image series from a current study with similar image series from three previous studies. Have three previous studies in the automatically created comparison layout is not required; there may be more or less previous studies depicted. Furthermore, in one embodiment, the layout generator uses a similarity threshold to determine if a series from a previously-created study is similar enough to be displayed. For example, if an image series from a previously-created study is less than a certain percentage similar (e.g., less than 80% similar, less than 70% similar, etc.), then that image series is not displayed on the screen.

In one embodiment, the image recognition algorithm not only specifies the most similar image series, it also calculates a similarity order or ranking of the similarity between the current displayed image series and the image series that are found in prior studies. In this way, the viewer can also display a list of similar series per study so that user can easily select the second/third most similar series for viewing if so desired.

Figure 9:
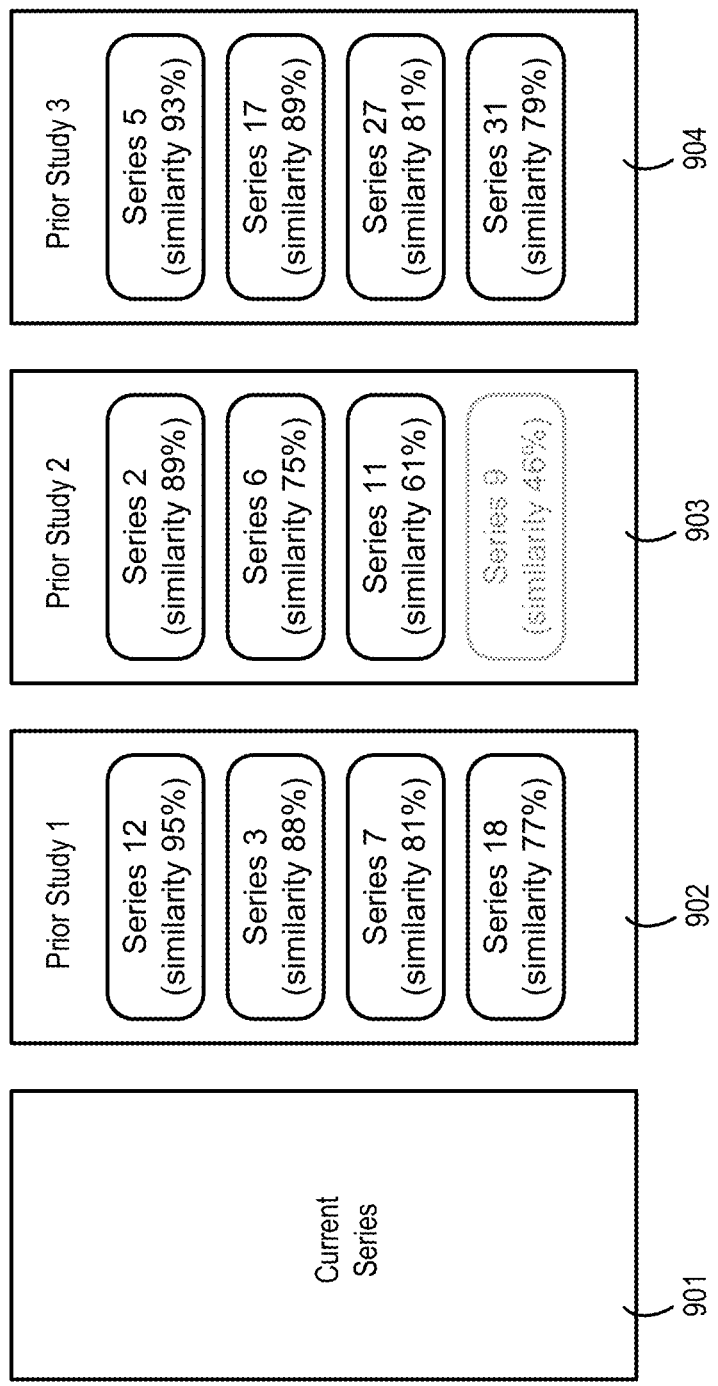
FIG. 9 illustrates an example of a display with ranked similarity that is generated by the layout generator component.

FIG. 9 illustrates an example of a display that is generated by the layout generator component that shows a series of current study 901 with windows showing prior studies 902-904, where series in each of studies 902-904 are ordered from top to bottom according to the level of similar that exists between a series and the current series of current study 901.

When an image or series contains electrocardiogram waveform data, the algorithm can display a video (that is multiple images played in series to create a video) while synchronizing the heart rate between at least two of the videos. The algorithm is capable of calculating similarity across multiple images or videos in series. The algorithm will also help synchronize the heart rate even if the electrocardiogram waveform is missing.

FIG. 10 is a flow diagram of one embodiment of a process for displaying series images in a graphical user interface (GUI). In one embodiment, the processes are performed by processing logic that may comprise hardware (circuitry, dedicated logic, etc.), software (e.g., software running on a chip), firmware, or a combination of the three. In one embodiment, the process is performed by a medical image management system having an image comparator, a layout generator, and a display.

Referring to FIG. 10, the process begins by processing logic receiving a current study and one or more previously-created studies, where each of the current study and the one or more previously-created studies having at least one images series (processing block 1001).

After receiving a current study and one or more previously-created studies, processing logic performs, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies (processing block 1002). In one embodiment, creating the comparison layout in the GUI with at least one image from one image series of the current study adjacent to at least one image from an image series of at least one of the one or more previously-created studies comprises synchronizing the at least one image from the image series of the at least one of the one or more previously-created studies to the at least one image from the one image series of the current study.

In one embodiment, performing the comparison between the at least one image series in the current study and the at least one image series in each of the one or more previously-created studies occurs in response to displaying one or more images of the current study.

In one embodiment, performing the comparison comprises calculating image similarity between a representative slice (image) in all series being compared. In one embodiment, performing the comparison comprises calculating image similarity between a slice in all series being compared that is located at a predetermined location in the series. In one embodiment, the slice is the middle slice of all the series.

After performing the comparison, processing logic creates a comparison layout in the GUI with at least one image from one image series of the current study adjacent to at least one image from an image series of at least one of the one or more previously-created studies (processing block 1003). In one embodiment, creating the comparison layout comprises automatically lining up a current image in the current study next to one or more previous study images in the one or more previous studies determined to be most similar to the current image based on results of performing the comparison.

In one embodiment, processing logic causes the display to display an amount of similarity on the GUI for one or more studies in the previously-created studies (processing block 1004).

FIG. 11 is a flow diagram of an alternative embodiment of a process for displaying series images in a graphical user interface (GUI). In one embodiment, the processes are performed by processing logic that may comprise hardware (circuitry, dedicated logic, etc.), software (e.g., software running on a chip), firmware, or a combination of the three. In one embodiment, the process is performed by a medical image management system having an image comparator, a layout generator, and a display.

Referring to FIG. 11, the process begins by processing logic receiving a current study and displaying at least one image from at least one image series in the study (processing block 1101).

In response to displaying the image from the current study, processing logic automatically obtains one or more previously-created studies in response to displaying one or more images of the current study (processing block 1102). Each of the current study and the one or more previously-created studies having at least one images series.

After receiving a current study and one or more previously-created studies, processing logic performs, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies (processing block 1103). In one embodiment, creating the comparison layout in the GUI with at least one image from one image series of the current study adjacent to at least one image from an image series of at least one of the one or more previously-created studies comprises synchronizing the at least one image from the image series of the at least one of the one or more previously-created studies to the at least one image from the one image series of the current study.

In one embodiment, performing the comparison between the at least one image series in the current study and the at least one image series in each of the one or more previously-created studies occurs in response to displaying one or more images of the current study.

In one embodiment, performing the comparison comprises calculating image similarity between a representative slice (image) in all series being compared. In one embodiment, performing the comparison comprises calculating image similarity between a slice in all series being compared that is located at a predetermined location in the series. In one embodiment, the slice is the middle slice of all the series.

Processing logic also generates a rank similarity order indicating comparative similarity between a plurality of image series of each of the previously-created studies and a current image series of the current study being viewed (processing block 1104).

After performing the comparison and generating the rank similarity, processing logic creates a comparison layout in the GUI with at least one image from one image series of the current study adjacent to at least one image from an image series of at least one of the one or more previously-created studies (processing block 1105). In one embodiment, creating the comparison layout comprises automatically lining up a current image in the current study next to one or more previous study images in the one or more previous studies determined to be most similar to the current image based on results of performing the comparison.

Processing logic also displays the ranking similarity order in the GUI with selectable user interface elements to enable selection of each ranked series in the previously-created studies to cause one or more images of a selected study to be displayed in the comparison layout with one or more images from the current study (processing block 1106).

An Exemplary Medical Imaging Management System

Figure 12:
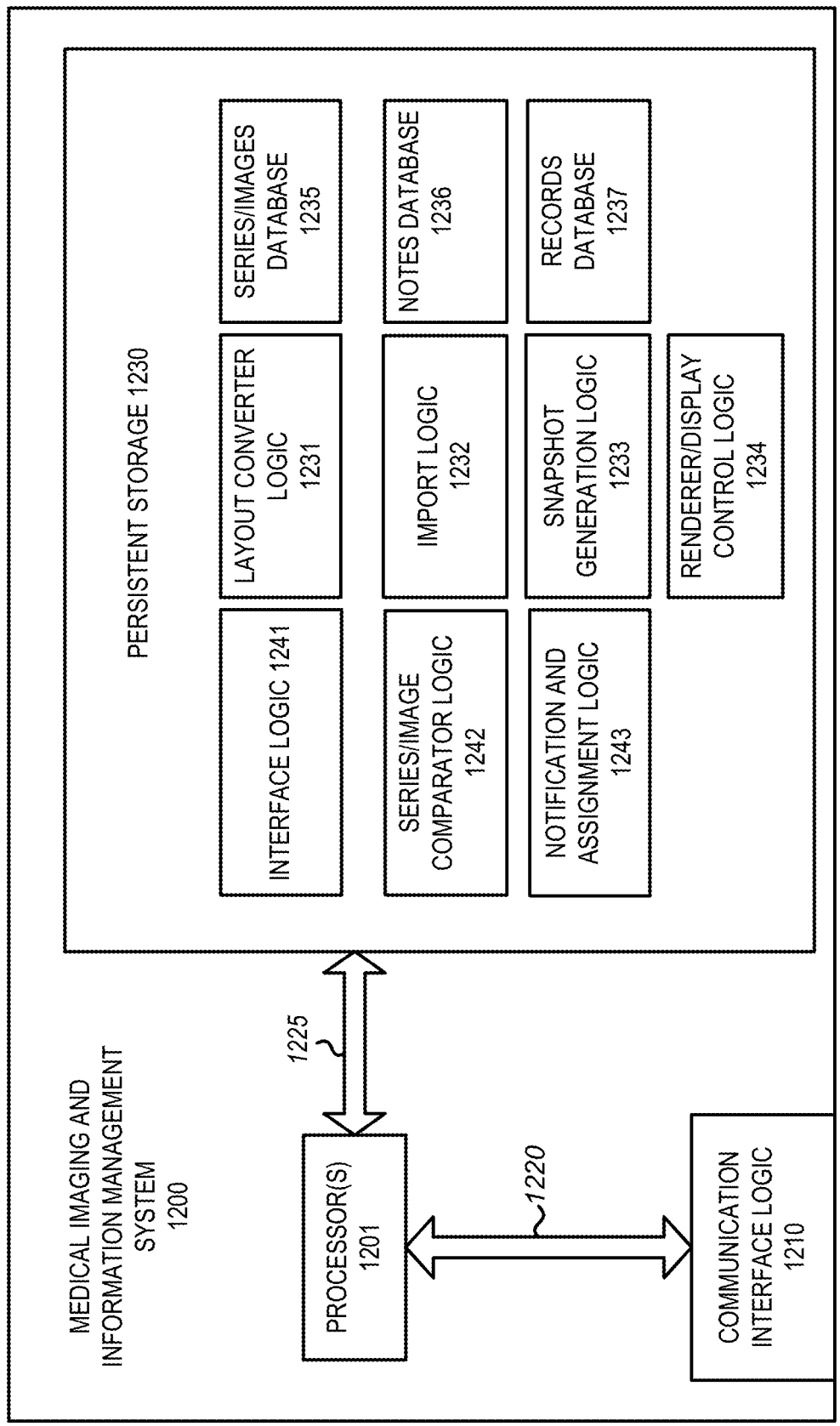
FIG. 12 illustrates an exemplary embodiment of a logical representation of a medical imaging and information management system that generates and renders image comparison layouts.

FIG. 12 illustrates an exemplary embodiment of a logical representation of a medical imaging and information management system 1200 that generates and renders image comparison layouts discussed above. The system performs matching of image series based on image similarity and automatically creates layouts with series images of a current study and one or more past (previously-created) studies. In one embodiment, system 1200 is part of a medical image system such as detailed above.

The medical imaging and information management system 1200 includes one or more processors 1201 that are coupled to communication interface logic 1210 via a first transmission medium 1220. The communication interface logic 1210 enables communications with other electronic devices, specifically enabling communication with remote users such as doctors, nurses and/or medical technicians, remote databases (e.g., PACS) that store healthcare studies, and healthcare modalities that generate and send studies. According to one embodiment of the disclosure, communication interface logic 1210 may be implemented as a physical interface including one or more ports for wired connectors. Additionally, or in the alternative, communication interface logic 1210 may be implemented with one or more radio units for supporting wireless communications with other electronic devices.

The processor(s) 1201 is further coupled to persistent storage 1230 via transmission medium 1225. According to one embodiment of the disclosure, persistent storage 1230 may include (a) user interface logic 1241, (b) series/image comparator logic 1242, (c) notification and assignment logic 1243, (d) layout generation logic 1231, (e) an import logic 1232, (f) a snapshot generation logic 1233, (g) a renderer/display control logic 1234, (h) an images database 1235, (i) a notes database 1236 and (j) a records database 1237.

The user interface logic 1241 may include logic for enabling interaction between a user and the display areas being displayed on the screen.

The series/image comparator logic 1242 includes logic for controlling the running an image recognition algorithm to determine image similarity between series images in multiple studies such as described above. In one embodiment, series/image comparator logic 1242 also determines a similarity ranking and/or determines an amount of similarity that exists between series images in multiple studies.

The notification and assignment logic 1243 includes logic to issue and send notifications and/or assignments for study reviews.

The import logic 1232 may include logic for retrieving one or more pieces of information from a storage device and importing each of the one or more pieces of information into a separate display area of a layout template. For example, the pieces of information may include, but are not limited or restricted to, (i) medical images, including x-rays, mammograms, computerized tomography (CT) scans, magnetic resonance imaging (MRI), positron emission tomography (PET) scan and/or ultrasound imaging, (ii) physician's notes regarding one or more of the medical images and/or (iii) medical records corresponding to one or more of the subjects of the one or more medical images.

The snapshot generation logic 1233 may include logic for saving at least a first state of the layout template. Saving the first state may include storing, at least, (i) the one or more pieces of information, and (ii) viewing properties of each of the one or more pieces of information in a non-transitory computer-readable medium. The layout template may depict a comparison layout depicting one or more images from a current study and one or more images determined to be similar from one or more previously-created studies.

The renderer/display control logic 1234 may include logic for creating a comparison layout template with one or more images from a series in a current study with images from series in one or more previously-created studies that were matched based on visual similarity.

Additionally, in one embodiment, the renderer/display control logic 1234 may include logic for displaying a rank order of the similarities for multiple image series that have been compared against an image series in the current study. Furthermore, in one embodiment, the renderer/display control logic 1234 may include logic for displaying an indication of how similar each series of the previously-created studies is with the series of the current study.

The images database 1235, the notes database 1236 and the records database 1237 may comprise a single non-transitory computer-readable medium storage device or may each be a separate non-transitory computer-readable medium storage device. The images database 1235 stores medical images that a user may import into a display area of a viewer or other GUI. The notes database 1236 stores notes recorded by a doctor, nurse, medical technician, etc., that a user may import into a display area of a layout template. Finally, the records database 1237 stores medical records that a user may import into a display area of a layout template.

There is a number of example embodiments described herein.

Example 1 is a method for displaying series images in a graphical user interface (GUI), where the method comprises: receiving a current study and one or more previously-created studies, each of the current study and the one or more previously-created studies having at least one images series; performing, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies; and creating a comparison layout in the GUI with at least one image from one image series of the current study adjacent to at least one image from an image series of at least one of the one or more previously-created studies.

Example 2 is the method of example 1 that may optionally include that performing the comparison comprises calculating image similarity between a representative slice in all series being compared.

Example 3 is the method of example 1 that may optionally include that performing the comparison comprises calculating image similarity between a slice in all series being compared that is located at a predetermined location in the series.

Example 4 is the method of example 1 that may optionally include that performing the comparison comprises calculating image similarity between a middle slice in all series being compared.

Example 5 is the method of example 1 that may optionally include that creating the comparison layout comprises automatically lining up a current image in the current study next to one or more previous study images in the one or more previous studies determined to be most similar to the current image based on results of performing the comparison.

Example 6 is the method of example 1 that may optionally include generating a rank similarity order indicating comparative similarity between a plurality of image series of each of the previously-created studies and a current image series of the current study being viewed; and displaying the ranking similarity order in the GUI with selectable user interface elements to enable selection of each ranked series in the previously-created studies to cause one or more images of a selected study to be displayed in the comparison layout with one or more images from the current study.

Example 7 is the method of example 1 that may optionally include displaying an amount of similarity on the GUI for one or more studies in the previously-created studies.

Example 8 is the method of example 1 that may optionally include automatically obtaining the one or more previously-created studies in response to displaying one or more images of the current study.

Example 9 is the method of example 1 that may optionally include that performing the comparison between the at least one image series in the current study and the at least one image series in each of the one or more previously-created studies occurs in response to displaying one or more images of the current study.

Example 10 is the method of example 1 that may optionally include that creating the comparison layout in the GUI with at least one image from one image series of the current study adjacent to at least one image from an image series of at least one of the one or more previously-created studies comprises synchronizing the at least one image from the image series of the at least one of the one or more previously-created studies to the at least one image from the one image series of the current study.

Example 11 is a non-transitory computer readable storage media having instructions stored thereupon which, when executed by a system having at least a processor and a memory therein, cause the system to perform a method for displaying series images in a graphical user interface (GUI), where the method comprises: receiving a current study and one or more previously-created studies, each of the current study and the one or more previously-created studies having at least one images series; performing, using one or more processors performing an image recognition routine, a comparison between at least one image series in the current study and at least one image series in each of the one or more previously-created studies by calculating image similarity between the at least one image series in the current study and the at least one image series of said each of the one or more previously-created studies; and creating a comparison layout in the GUI with at least one image from one image series of the current study adjacent to at least one image from an image series of at least one of the one or more previously-created studies.

Example 12 is the computer readable storage media of example 11 that may optionally include that performing the comparison comprises calculating image similarity between a representative slice in all series being compared.

Example 13 is the computer readable storage media of example 11 that may optionally include that performing the comparison comprises calculating image similarity between a slice in all series being compared that is located at a predetermined location in the series.

Example 14 is the computer readable storage media of example 11 that may optionally include that performing the comparison comprises calculating image similarity between a middle slice in all series being compared.

Example 15 is the computer readable storage media of example 11 that may optionally include that creating the comparison layout comprises automatically lining up a current image in the current study next to one or more previous study images in the one or more previous studies determined to be most similar to the current image based on results of performing the comparison.

Example 16 is the computer readable storage media of example 11 that may optionally include generating a rank similarity order indicating comparative similarity between a plurality of image series of each of the previously-created studies and a current image series of the current study being viewed; and displaying the ranking similarity order in the GUI with selectable user interface elements to enable selection of each ranked series in the previously-created studies to cause one or more images of a selected study to be displayed in the comparison layout with one or more images from the current study.

Example 17 is an apparatus comprising a network communication interface to receive a current study and one or more previously-created studies, each of the current study and the one or more previously-created studies having at least one images series; an image comparator coupled to the communication interface and implemented with one or more processors that are operable to perform an image comparison between at least one image series in the current study and at least one image series in each of the one or more previously-created studies by calculating image similarity between the at least one image series in the current study and the at least one image series of said each of the one or more previously-created studies; and an image renderer coupled to the image comparator and operable to create a comparison layout in the GUI with at least one image from one image series of the current study adjacent to at least one image from an image series of at least one of the one or more previously-created studies.

Example 18 is the apparatus of example 11 that may optionally include that the image comparator performs the comparison by calculating image similarity between a representative slice in all series being compared.

Example 19 is the apparatus of example 11 that may optionally include that the image comparator performs the comparison by calculating image similarity between a slice in all series being compared that is located at a predetermined location in the series.

Example 20 is the apparatus of example 11 that may optionally include that the image comparator performs the comparison by calculating image similarity between a middle slice in all series being compared.

Example 21 is the apparatus of example 11 that may optionally include that image renderer is operable to create the comparison layout by automatically lining up a current image in the current study next to one or more previous study images in the one or more previous studies determined to be most similar to the current image based on results of performing the comparison.

Example 22 is the apparatus of example 11 that may optionally include a rank component coupled to the image comparator and operable to generate a rank similarity order indicating comparative similarity between a plurality of image series of each of the previously-created studies and a current image series of the current study being viewed, wherein the image renderer is operable to display the ranking similarity order in the GUI with selectable user interface elements to enable selection of each ranked series in the previously-created studies to cause one or more images of a selected study to be displayed in the comparison layout with one or more images from the current study.

Example 23 is the apparatus of example 11 that may optionally include that the image renderer is operable to display an amount of similarity on the GUI for one or more studies in the previously-created studies.

Example 24 is the apparatus of example 11 that may optionally include that the network communication interface is instructed automatically to obtain the one or more previously-created studies in response to displaying one or more images of the current study.

Example 25 is the apparatus of example 11 that may optionally include that the image comparator performs the comparison between the at least one image series in the current study and the at least one image series in each of the one or more previously-created studies in response to displaying one or more images of the current study.

Example 26 is the apparatus of example 11 that may optionally include that image renderer is operable to create the comparison layout in the GUI with at least one image from one image series of the current study adjacent to at least one image from an image series of at least one of the one or more previously-created studies by synchronizing the at least one image from the image series of the at least one of the one or more previously-created studies to the at least one image from the one image series of the current study.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

I claim:

1. A method comprising:
   receiving, by one or more processors, a current study and one or more previously-created studies, each of the current study and the one or more previously-created studies having at least one image series, wherein each image series comprises more than one image, wherein each image comprises waveform data;
   based on the receiving, displaying, by the one or more processors, the at least one image series of the current study in the GUI;
   responsive to the displaying, automatically performing, by the one or more processors, an image recognition routine comprising:
   comparing at least one image series in the current study to at least one image series in each of the one or more previously-created studies; and
   calculating image similarity between the at least one image series in the current study and the at least one image series of each previously-created study of the one or more previously-created studies, based on applying an algorithm;
   generating, by the one or more processors, a rank similarity order indicating comparative similarity between a plurality of image series of each of the previously-created studies and a current image series of the current study being viewed; and
   creating, by one or more processors, a comparison layout in the GUI with at least one image from one image series of the current study adjacent to at least one image from an image series of at least one of the one or more previously-created studies, wherein creating the comparison layout comprises, based on the algorithm results, synchronizing waveform data of each image of the at least one image from the one image series of the current study adjacent and the at least one image from the an image series of the at least one of the one or more previously-created studies.

2. The method defined in claim 1, wherein comparing the at least one image series in the current study to the at least one image series in each of the one or more previously-created studies comprises calculating image similarity between a representative slice in all series being compared.

3. The method defined in claim 1, wherein comparing the at least one image series in the current study to the at least one image series in each of the one or more previously-created studies comprises calculating image similarity between a slice in all series being compared that is located at a predetermined location in the series.

4. The method defined in claim 1, wherein comparing the at least one image series in the current study to the at least one image series in each of the one or more previously-created studies comprises calculating image similarity between a middle slice in all series being compared.

5. The method defined in claim 1, wherein creating the comparison layout comprises automatically lining up a current image in the current study next to one or more previous study images in the one or more previous studies determined to be most similar to the current image based on results of performing the comparison.

6. The method defined in claim 1, further comprising:
   displaying the ranking similarity order in the GUI with selectable user interface elements to enable selection of each ranked series in the previously-created studies to cause one or more images of a selected study to be displayed in the comparison layout with one or more images from the current study, wherein the displaying comprises displaying video of the synchronized waveform data, wherein the video comprises a portion of the images of the at least one image from the one image series of the current study adjacent and the at least one image from the an image series of the at least one of the one or more previously-created studies, played in a series.

7. The method defined in claim 1, further comprising: displaying an amount of similarity on the GUI for one or more studies in the previously-created studies.

8. The method defined in claim 1, wherein creating the comparison layout in the GUI with at least one image from one image series of the current study adjacent to at least one image from an image series of at least one of the one or more previously-created studies comprises synchronizing the at least one image from the image series of the at least one of the one or more previously-created studies to the at least one image from the one image series of the current study.

9. The method of claim 6, wherein the waveform data comprises electrocardiogram waveform data, and wherein synchronizing the waveform data comprises synchronizing a heart rate.

10. A non-transitory computer readable storage media having instructions stored thereupon which, when executed by a system having one or more processors and a memory therein, cause the system to perform a method for displaying series images in a graphical user interface (GUI), the method comprising:
receiving, by the one or more processors, a current study and one or more previously-created studies, each of the current study and the one or more previously-created studies having at least one image series, wherein each image series comprises more than one image, wherein each image comprises waveform data;
based on the receiving, displaying, by the one or more processors, the at least one image series of the current study in the GUI;
responsive to the displaying, automatically performing, by the one or more processors, an image recognition routine comprising:
comparing at least one image series in the current study to at least one image series in each of the one or more previously-created studies; and
calculating image similarity between the at least one image series in the current study and the at least one image series of each previously-created study of the one or more previously-created studies, based on applying an algorithm;
generating, by the one or more processors, a rank similarity order indicating comparative similarity between a plurality of image series of each of the previously-created studies and a current image series of the current study being viewed; and
creating, by one or more processors, a comparison layout in the GUI with at least one image from one image series of the current study adjacent to at least one image from an image series of at least one of the one or more previously-created studies, wherein creating the comparison layout comprises, based on the algorithm results, synchronizing waveform data of each image of the at least one image from the one image series of the current study adjacent and the at least one image from the an image series of the at least one of the one or more previously-created studies.

11. The method defined in claim 10, wherein comparing the at least one image series in the current study to the at least one image series in each of the one or more previously-created studies comprises calculating image similarity between a representative slice in all series being compared.

12. The method defined in claim 10, wherein comparing the at least one image series in the current study to the at least one image series in each of the one or more previously-created studies comprises calculating image similarity between a slice in all series being compared that is located at a predetermined location in the series.

13. The method defined in claim 10, wherein comparing the at least one image series in the current study to the at least one image series in each of the one or more previously-created studies comprises calculating image similarity between a middle slice in all series being compared.

14. The method defined in claim 10, wherein creating the comparison layout comprises automatically lining up a current image in the current study next to one or more previous study images in the one or more previous studies determined to be most similar to the current image based on results of performing the comparison.

15. The method defined in claim 10, further comprising:
displaying the ranking similarity order in the GUI with selectable user interface elements to enable selection of each ranked series in the previously-created studies to cause one or more images of a selected study to be displayed in the comparison layout with one or more images from the current study, wherein the displaying comprises displaying video of the synchronized waveform data, wherein the video comprises a portion of the images of the at least one image from the one image series of the current study adjacent and the at least one image from the an image series of the at least one of the one or more previously-created studies, played in a series.

16. An apparatus comprising:
a network communication interface to receive a current study and one or more previously-created studies, each of the current study and the one or more previously-created studies having at least one image series, wherein each image series comprises more than one image, wherein each image comprises waveform data; and
an image renderer, coupled to the network communication interface, to display the at least one image series of the current study in a graphical user interface, based on the network communication interface receiving the current study and the one or more previously-created studies;
an image comparator coupled to the communication interface and implemented with one or more processors that are operable to automatically perform an image recognition routine, based on the image renderer displaying the current study in the GUI, wherein the image recognition routine comprises: the image comparator comparing at least one image series in the current study to at least one image series in each of the one or more previously-created studies and calculating image similarity between the at least one image series in the current study and the at least one image series of each previously-created study of the one or more previously-created studies, based on applying an algorithm;
a rank component coupled to the image comparator and operable to generate a rank similarity order indicating comparative similarity between a plurality of image series of each of the previously-created studies and a current image series of the current study being viewed; and
the image renderer coupled to the image comparator and operable to create a comparison layout in the GUI with at least one image from one image series of the current study adjacent to at least one image from an image series of at least one of the one or more previously-created studies, wherein creating the comparison layout comprises, based on the algorithm results, synchronizing waveform data of each image of the at least one image from the one image series of the current study adjacent and the at least one image from the an image series of the at least one of the one or more previously-created studies.

17. The apparatus defined in claim 16, wherein the image comparator compares the at least one image series in the current study to the at least one image series in each of the one or more previously-created studies by calculating image similarity between a representative slice in all series being compared.

18. The apparatus defined in claim 16, wherein the image comparator compares the at least one image series in the current study to the at least one image series in each of the one or more previously-created studies by calculating image similarity between a slice in all series being compared that is located at a predetermined location in the series.

19. The apparatus defined in claim 16, wherein the image comparator compares the at least one image series in the current study to the at least one image series in each of the one or more previously-created studies by calculating image similarity between a middle slice in all series being compared.

20. The apparatus defined in claim 16, wherein image renderer is operable to create the comparison layout by automatically lining up a current image in the current study next to one or more previous study images in the one or more previous studies determined to be most similar to the current image based on results of performing the comparison.

21. The apparatus defined in claim 16, wherein the image renderer is operable to display the ranking similarity order in the GUI with selectable user interface elements to enable selection of each ranked series in the previously-created studies to cause one or more images of a selected study to be displayed in the comparison layout with one or more images from the current study, wherein the displaying comprises displaying video of the synchronized waveform data, wherein the video comprises a portion of the images of the at least one image from the one image series of the current study adjacent and the at least one image from the an image series of the at least one of the one or more previously-created studies, played in a series.

22. The apparatus defined in claim 16, wherein the image renderer is operable to display an amount of similarity on the GUI for one or more studies in the previously-created studies.

23. The apparatus defined in claim 16, wherein the network communication interface is instructed automatically to obtain the one or more previously-created studies in response to displaying one or more images of the current study.

24. The apparatus defined in claim 16, wherein the image comparator performs the comparison between the at least one image series in the current study and the at least one image series in each of the one or more previously-created studies in response to displaying one or more images of the current study.

25. The apparatus defined in claim 16, wherein the image renderer is operable to create the comparison layout in the GUI with at least one image from one image series of the current study adjacent to at least one image from an image series of at least one of the one or more previously-created studies by synchronizing the at least one image from the image series of the at least one of the one or more previously-created studies to the at least one image from the one image series of the current study.

\* \* \* \* \*